United States Patent [19]

Dahle, deceased

[11] 4,104,053
[45] Aug. 1, 1978

[54] 3-BENZYL-2-METHYLIMINO-5-PHENYL-$\Delta^4$-1,3,4-THIADIAZOLINES AND METHOD OF COMBATING UNDESIRED PLANT GROWTH

[75] Inventor: Norman A. Dahle, deceased, late of Lenexa, Kans.

[73] Assignee: Gulf Oil Corporation, Pittsburgh, Pa.

[21] Appl. No.: 503,211

[22] Filed: Sep. 4, 1974

[51] Int. Cl.$^2$ .............................................. A01N 9/22
[52] U.S. Cl. ................................ 71/90; 260/306.8 D
[58] Field of Search ........................................... 71/90

[56] References Cited

U.S. PATENT DOCUMENTS

| 3,282,950 | 11/1966 | Ottmann et al. | 71/90 |
| 3,429,688 | 2/1969 | Duerr et al. | 71/90 |
| 3,801,589 | 4/1974 | Sasse et al. | 71/90 |

Primary Examiner—Glennon H. Hollrah
Attorney, Agent, or Firm—Carl A. Cline

[57] ABSTRACT

A class of 3-benzyl-2-methylimino-5-phenyl-$\Delta^4$-1,3,4-thiadiazolines which may have certain specific substituents on the benzyl and phenyl rings are useful in combating various weeds in grain crops, for example, grassy weeds in wheat and rice fields.

11 Claims, No Drawings

3-BENZYL-2-METHYLIMINO-5-PHENYL-Δ⁴-1,3,4-THIADIAZOLINES AND METHOD OF COMBATING UNDESIRED PLANT GROWTH

DESCRIPTION OF THE INVENTION

A class of tautomeric alkyliminothiadiazolines has been disclosed in U.S. Pat. No. 3,522,267 to be useful as herbicides, one compound being disclosed to be particularly useful for combating weeds in root crops, such as sugarbeets or onions.

I have discovered that a novel class of nontautomeric methyliminothiadiazolines have distinctly different phytotoxic selectivity and are particularly useful in combating weeds in grains, particularly in wheat and rice fields, being effective at application rates of less than 4 lb per acre (4.5 kg. per hectare). The novel herbicidal agents are effective against broadleaf weeds belonging to families of which sugar beets, radishes, tomato, alfalfa and coxcomb are representative species, as well as many pestiferous grasses.

Briefly, my method of combating weeds in grain fields comprises applying to the area where the combating effect is desired a herbicidally effective amount of a compound of the formula:

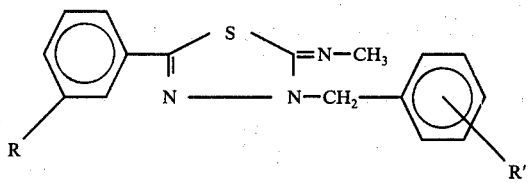

in which R is methyl or chloro and R' is hydrogen, methyl, trifluoromethyl, benzyloxy, chloro or fluoro, said compound being applied either in unmodified form or in the form of a salt with an acid, in combination with a carrier. Water is a preferred carrier, although other liquid and finely divided solid carriers may be used.

Preparation of the Herbicides

The compounds of this invention may be prepared from commercially available intermediates by means of the procedures which are specifically exemplified below.

2-Methylamino-5-(3-chlorophenyl)-1,3,4-thiadiazole

A well-stirred mixture of 125 g (0.8 mole) of 3-chlorobenzoic acid and 84 g (0.8 mole) of 4-methylthiosemicarbazide in 700 ml of dioxane was heated until the solution was homogeneous. Phosphorus oxychloride (123 g, 0.8 mole) was added dropwise to the resulting solution at a rate to maintain the dioxane at gentle reflux.

After the addition was completed, the mixture was heated at reflux an additional 45 minutes. The reaction mixture was allowed to cool to room temperature and the dioxane was decanted into 1,000 ml of 13 percent aqueous sodium hydroxide solution. The remaining insoluble mass was transferred to a mortar where it was pulverized. The powdered material was added to the aqueous sodium hydroxide-dioxane mixture and the latter was allowed to stir at room temperature for 150 min. Sufficient water was added to the mixture to produce a final volume of 3,500 ml. The solution was allowed to stir at room temperature for 75 min. and the insoluble material was collected on a Buchner funnel. Recrystallization of the crude product from 95 percent ethanol afforded 108 g of the desired product. m.p. 141°-43°.

2-Methylimino-3-(4-methylbenzyl)-5-(3-chlorophenyl)-Δ⁴-1,3,4-thiadiazoline

A well-stirred mixture of 150.0 g (0.67 mole) of 2-methylamino-5-(3-chlorophenyl)-1,3,4-thiadiazole, 150.0 g (1.07 mole) of α-chloro-p-xylene and 300 ml of dioxane were heated at reflux for 24 hr. The reaction mixture was cooled and approximately 400 ml of hexane was added. The insoluble material was separated by vacuum filtration. The crude salt was added to 600 ml of 10% methanolic potassium hydroxide. The mixture was allowed to stir at room temperature for 24 hr. The resulting solution was diluted to 3,000 ml with water and the insoluble material was separated by filtration. Recrystallization of the crude material gave 182 g of the title compound. m.p. 94°-97°.

Preparation of the hydrochloride salt of 2-methylimino-3-benzyl-5-(3-chlorophenyl)-Δ⁴-1,3,4-thiadiazoline A well stirred mixture of 13.0 g (0.058 mole) of 2-methylamino-5-(3-chlorophenyl)-1,3,4-thiadiazole, 13.0 g (0.10 mole) of benzyl chloride and 25 ml of dioxane were heated at reflux for 18 hr. The reaction mixture was cooled, treated with 30 ml of hexane and the insoluble material collected by vacuum filtration. The crude product was recrystallized from a mixture of chloroform-hexane to afford 11.5 g of the desired compound. m.p. 96°-98°.

Preparation of the trichloroacetic acid salt of 2-methylimino-3-benzyl-5-(3-chlorophenyl)-Δ⁴-1,3,4-thiadiazoline To a cold solution of 8.0 g (0.025 mole) 2-methylimino-3-benzyl-5-(3-chlorophenyl)-Δ⁴-1,3,4-thiadiazoline in 25 ml of benzene was added a solution of 4.1 g (0.025 mole) of trichloroacetic acid in 20 ml of benzene. The mixture was allowed to stir at room temperature for 60 minutes and the resulting insoluble material was separated by filtration, affording 11.0 g of the desired salt with a melting point 107°-08°.

Compounds which have been prepared by the above-described procedures are listed in Table 1.

TABLE I
COMPOUNDS OF THE FORMULA

| Compound Number | R | R' | | m.p.°C or (BP °C/mm Hg) |
|---|---|---|---|---|
| 1 | chloro | hydrogen | | 72-73 |
| 2 | chloro | 3-methyl | | 77-78 |
| 3 | chloro | 4-methyl | | 92-94 |
| 4 | methyl | 3-chloro | | 78-80 |
| 5 | methyl | 4-methyl | | oil at room temp. |
| 6 | chloro | 3-fluoro | | 77-79 |
| 7 | chloro | 4-fluoro | | 98-100 |
| 8 | methyl | 4-fluoro | (HCl salt) | 194-96 |
| 9 | methyl | 4-fluoro | | 53-54 |
| 10 | methyl | 3-trifluoromethyl | (HCl salt) | 193-94 |

TABLE I-continued

COMPOUNDS OF THE FORMULA

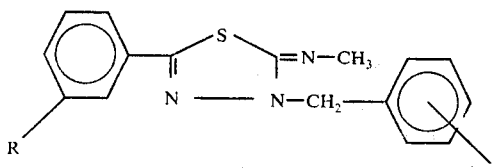

| Compound Number | R | R' | | m.p.C° or (BP °C/mm Hg) |
|---|---|---|---|---|
| 11 | methyl | 3-trifluoromethyl | | oil at room temp. |
| 12 | chloro | hydrogen | (HCl salt) | 196-98 |
| 13 | chloro | 3-trifluoromethyl | (HCl salt) | 206-08 |
| 14 | chloro | 3-trifluoromethyl | | 98-101 |
| 15 | chloro | 4-methyl | (HCl salt) | 193-96 |
| 16 | chloro | 3-fluoro | (HCl salt) | 203-05 |
| 17 | chloro | hydrogen | (CCl$_3$CO$_2$H salt) | 107-08 |
| 18 | chloro | 4-benzyloxy | | 121-123 |
| 19 | methyl | 4-benzyloxy | | 91-93 |

Use of the Herbicides to Combat Weeds

Rice was grown in 4 inch Tufflite (polystyrene foam) pots placed on electric heating mats. The weed species were grown in 12 inch × 3 inch Tufflite flats. Greenhouse potting soil was used in both pots and flats.

Each herbicide was formulated for application by mixing with a solvent-emulsifier mixture to form a water-dispersible concentrate to which water was then added to form a spray mixture. The solvent emulsifier mixture consisted of 60 percent of a commercial emulsifier sold for agricultural use, 20 percent xylene and 20 percent kerosene.

The compounds were applied to various rates, both pre- and post-emergently to different pots and flats at the same time. Application was made at a spray volume of 40 gal/A with a 6501 nozzle. Herbicides were incorporated in the soil in pre-emergent tests by adding one-fourth inch of soil over the sprayed surface. The tests were evaluated four weeks after spraying.

The results were scored on the following numerical scale:

0 = no observable injury
1 = temporary injury
2 = some permanent injury
3 = severe injury, some plants died
4 = all plants died The results are tabulated in Table II.

TABLE II

EFFECT OF HERBICIDES ON RICE AND WEEDS

| Compound no. | Appl'n Rate (lb/A) | Crabgrass Digitaria sanguinalis | green sprangletop Leptochloa dubia | barnyard grass Echinochloa crusgalli | yellow foxtail Setaria glauca | smartweed Polygonum pennsylvanicum | rice Oryza sativa |
|---|---|---|---|---|---|---|---|
| 1 | Pre-Emergent | | | | | | |
| | 4 | 4 | 4 | 4 | 4 | 2 | 1 |
| | 1 | 4 | 4 | 4 | 4 | 1 | 0 |
| | ½ | 4 | 4 | 3 | 4 | 1 | 0 |
| | ¼ | 2 | 1 | 1 | 2 | 0 | 0 |
| | Post-Emergent | | | | | | |
| | 4 | 4 | 4 | 4 | 4 | 4 | 2 |
| | 1 | 4 | 4 | 4 | 4 | 4 | 0 |
| | ½ | 4 | 4 | 4 | 4 | 3 | 0 |
| | ¼ | 4 | 4 | 4 | 4 | 2 | 0 |
| 2 | Pre-Emergent | | | | | | |
| | 4 | 4 | 4 | 4 | 4 | 1 | 1 |
| | 1 | 4 | 4 | 3 | 4 | 1 | 0 |
| | ½ | 3 | 3 | 2 | 4 | 0 | 0 |
| | ¼ | 1 | 1 | 1 | 2 | 0 | 0 |
| | Post-Emergent | | | | | | |
| | 4 | 4 | 4 | 4 | 4 | 4 | 1 |
| | 1 | 4 | 4 | 4 | 4 | 3 | 0 |
| | ½ | 4 | 4 | 4 | 4 | 2 | 0 |
| | ¼ | 4 | 4 | 3 | 4 | 2 | 0 |
| 3 | Pre-Emergent | | | | | | |
| | 4 | 4 | 4 | 4 | 4 | 2 | 2 |
| | 1 | 4 | 4 | 4 | 4 | 2 | 0 |
| | ½ | 4 | 4 | 3 | 4 | 1 | 0 |
| | ¼ | 3 | 3 | 2 | 3 | 0 | 0 |
| | Post-Emergent | | | | | | |
| | 4 | 4 | 4 | 4 | 4 | 4 | 2 |
| | 1 | 4 | 4 | 4 | 4 | 4 | 0 |
| | ½ | 4 | 4 | 4 | 4 | 3 | 0 |
| | ¼ | 4 | 4 | 4 | 4 | 2 | 0 |
| 4 | Pre-Emergent | | | | | | |
| | 4 | 4 | 4 | 4 | 4 | 3 | 1 |
| | 1 | 4 | 3 | 4 | 4 | 1 | 0 |
| | ½ | 3 | 4 | 2 | 4 | 1 | |
| | ¼ | 1 | 1 | 0 | 2 | 0 | 0 |
| | Post-Emergent | | | | | | |
| | 4 | 4 | 4 | 4 | 4 | 4 | 1 |
| | 1 | 4 | 4 | 4 | 4 | 3 | 0 |
| | ½ | 4 | 4 | 4 | 4 | 3 | 0 |
| | ¼ | 4 | 4 | 3 | 4 | 2 | — |

TABLE II-continued
EFFECT OF HERBICIDES ON RICE AND WEEDS

| Compound no. | Appl'n Rate (lb/A) | Crabgrass Digitaria sanguinalis | green sprangletop Leptochloa dubia | barnyard grass Echinochloa crusgalli | yellow foxtail Setaria glauca | smartweed Polygonum pennsylvanicum | rice Oryza sativa |
|---|---|---|---|---|---|---|---|
| 5 | Pre-Emergent | | | | | | |
|  | 4 | 4 | 4 | 4 | 4 | 3 | 1 |
|  | 1 | 4 | 4 | 3 | 4 | 1 | 0 |
|  | ½ | 2 | 4 | 2 | 3 | 0 | 0 |
|  | ¼ | 1 | 1 | 1 | 2 | 0 | 0 |
|  | Post-Emergent | | | | | | |
|  | 4 | 4 | 4 | 4 | 4 | 4 | 2 |
|  | 1 | 4 | 4 | 4 | 4 | 3 | 0 |
|  | ½ | 4 | 4 | 4 | 4 | 3 | 0 |
|  | ¼ | 4 | 4 | 3 | 3 | 2 | — |
| 6 | Pre-Emergent | | | | | | |
|  | 4 | 4 | 4 | 4 | 4 | 3 | 2 |
|  | 1 | 4 | 4 | 4 | 4 | 1 | 0 |
|  | ½ | 4 | 4 | 3 | 4 | 1 | 0 |
|  | ¼ | 3 | 4 | 2 | 3 | 0 | 0 |
|  | Post-Emergent | | | | | | |
|  | 4 | 4 | 4 | 4 | 4 | 4 | 1 |
|  | 1 | 4 | 4 | 4 | 4 | 4 | 1 |
|  | ½ | 4 | 4 | 4 | 4 | 3 | 0 |
|  | ¼ | 4 | 4 | 4 | 4 | 2 | 0 |
| 7 | Pre-Emergent | | | | | | |
|  | 4 | 4 | 4 | 4 | 4 | 2 | 1 |
|  | 1 | 4 | 4 | 4 | 4 | 2 | 0 |
|  | ½ | 3 | 4 | 3 | 4 | 0 | 0 |
|  | ¼ | 2 | 4 | 2 | 3 | 0 | 0 |
|  | Post-Emergent | | | | | | |
|  | 4 | 4 | 4 | 4 | 4 | 4 | 1 |
|  | 1 | 4 | 4 | 4 | 4 | 3 | 0 |
|  | ½ | 4 | 4 | 4 | 4 | 2 | 0 |
|  | ¼ | 4 | 4 | 3 | 3 | 1 | 0 |
| 8 | Pre-Emergent | | | | | | |
|  | 2 | 4 | | 4 | | 1 | 0 |
|  | 1 | 2 | | 4 | | 0 | 0 |
|  | ½ | 1 | | 2 | | 0 | 0 |
|  | Post-Emergent | | | | | | |
|  | 2 | 4 | | 4 | | 2 | 2 |
|  | 1 | 2 | | 3 | | 1 | 0 |
|  | ½ | 2 | | 2 | | 0 | 0 |
| 9 | Pre-Emergent | | | | | | |
|  | 2 | 4 | | 4 | | 1 | 0 |
|  | 1 | 3 | | 3 | | 1 | 0 |
|  | ½ | 0 | | 1 | | 0 | 0 |
|  | Post-Emergent | | | | | | |
|  | 2 | 4 | | 4 | | 2 | 1 |
|  | 1 | 3 | | 3 | | 1 | 1 |
|  | ½ | 1 | | 1 | | 0 | 0 |
| 10 | Pre-Emergent | | | | | | |
|  | 2 | 4 | 4 | 4 | | 3 | 1 |
|  | 1 | 4 | 3 | 4 | | 1 | 0 |
|  | ½ | 3 | 2 | 4 | | 0 | 0 |
|  | Post-Emergent | | | | | | |
|  | 2 | 4 | | 4 | | 4 | 1 |
|  | 1 | 4 | | 4 | | 3 | 0 |
|  | ½ | 2 | | 4 | | 2 | 0 |
| 11 | Pre-Emergent | | | | | | |
|  | 2 | 4 | 4 | 4 | | 3 | 1 |
|  | 1 | 4 | 4 | 4 | | 2 | 0 |
|  | ½ | 4 | 3 | 4 | | 2 | 0 |
|  | Post-Emergent | | | | | | |
|  | 2 | 4 | | 4 | | 4 | 2 |
|  | 1 | 4 | | 4 | | 3 | 0 |
|  | ½ | 3 | | 4 | | 2 | 0 |
| 12 | Pre-Emergent | | | | | | |
|  | 2 | 3 | 3 | 4 | | 1 | 0 |
|  | 1 | 1 | 3 | 2 | | 0 | 0 |
|  | ½ | 1 | 1 | 1 | | 0 | 0 |
|  | Post-Emergent | | | | | | |
|  | 2 | 3 | | 4 | | 1 | 1 |
|  | 1 | 2 | | 4 | | 2 | 0 |
|  | ½ | 3 | | 4 | | 1 | 0 |
| 13 | Pre-Emergent | | | | | | |

TABLE II-continued
EFFECT OF HERBICIDES ON RICE AND WEEDS

| Compound no. | Appl'n Rate (lb/A) | Crabgrass Digitaria sanguinalis | green sprangletop Leptochloa dubia | barnyard grass Echinochloa crusgalli | yellow foxtail Setaria glauca | smartweed Polygonum pennsylvanicum | rice Oryza sativa |
|---|---|---|---|---|---|---|---|
| | 2 | 4 | 4 | 4 | | 1 | 0 |
| | 1 | 3 | 4 | 3 | | 0 | 0 |
| | ½ | 2 | 4 | 2 | | 0 | 0 |
| | Post-Emergent | | | | | | |
| | 2 | 3 | | 4 | | 2 | 0 |
| | 1 | 2 | | 3 | | 2 | 0 |
| | ½ | 1 | | 3 | | 0 | 0 |
| 14 | Pre-Emergent | | | | | | |
| | 2 | 4 | 4 | 4 | | 1 | 0 |
| | 1 | 4 | 4 | 3 | | 0 | 0 |
| | ½ | 1 | 3 | 2 | | 0 | 0 |
| | Post-Emergent | | | | | | |
| | 2 | 3 | | 4 | | 3 | 1 |
| | 1 | 2 | | 4 | | 1 | 0 |
| | ½ | 1 | | 3 | | 0 | 0 |
| 15 | Pre-Emergent | | | | | | |
| | 2 | 4 | | 4 | | 2 | 1 |
| | 1 | 3 | | 3 | | 3 | 0 |
| | ½ | 1 | | 2 | | 0 | 0 |
| | Post-Emergent | | | | | | |
| | 2 | 3 | | 4 | | 3 | 1 |
| | 1 | 1 | | 1 | | 0 | 0 |
| | ½ | 1 | | 0 | | 0 | 0 |
| 17 | Pre-Emergent | | | | | | |
| | 2 | 4 | 4 | 4 | | 3 | 1 |
| | 1 | 4 | 4 | 4 | | 2 | 0 |
| | ½ | 1 | 3 | 4 | | 0 | 0 |
| | Post-Emergent | | | | | | |
| | 2 | 4 | | 4 | | 4 | 1 |
| | 1 | 4 | | 4 | | 2 | 1 |
| | ½ | 2 | | 4 | | 1 | 0 |

The herbicides of this invention do not present unique formulation problems and may be readily formulated by conventional techniques, employing solvents, diluents, solid carriers and surface active agents which are commercially available and are approved for agricultural use. The herbicides of this invention are all nitrogen bases which readily form salts with strong acids and in fact are most conveniently prepared as hydrohalide salts. They may be formulated and applied in salt form if it is more convenient to do so. However, by converting the salt form to the free base as illustrated in procedures disclosed above, a product is obtained which is soluble in a greater variety of organic solvents. This may be considered more desirable from the standpoint of formulation economy. It should be kept in mind that the salt form has a greater weight, mole for mole, than the free base and this must be taken into account in formulating to a desired concentration of active agent.

Some of the compounds listed in Table I have outstanding utility of certain specific types. Compounds numbered 1, 9, 12 and 16 may be used to particular advantage in combination with the commercial herbicide barban to give broad spectrum weed control in wheat. Compounds numbered 18 and 19 are broadly useful in combating weeds in a number of small grain crops, including wheat, oats and rice. The latter two compounds are readily prepared by the reaction of the commercially available 4-benzyloxybenzyl chloride with either 2-methylamino-5-(3-methylphenyl)-1,3,4-thiadiazole or 2-methylamine-5-(3-chlorophenyl)-1,3,4-thiadiazole by procedures described above. The reaction is conveniently carried out in refluxing dioxane as a reaction solvent, followed by neutralization of the resulting mixture with methanolic sodium hydroxide and recovery of the product as in the procedure exemplified above for the corresponding 4-methylbenzyl compound. The compounds mentioned above which have specific utility for weed control in wheat were evaluated in the greenhouse in comparative tests on wheat and five associated weed species by the procedure described above and results were rated according to the same schedule employed in Table II. The results appear below in Tables III and IV. In areas in which sugar beets, rape and small grains are grown, a small group of particularly troublesome weeds and volunteer crop plants often flourish in competition with the crops and each other. Compounds 18 and 19 were used pre-emergently according to above-described procedures on sugar beets, rape and a small number of associated weeds. Results appear in Table V.

TABLE III
EFFECT OF HERBICIDES ON WHEAT AND ASSOCIATED WEEDS

| Compound no. | Application Rate (lb/A) | Pigweed Amaranthus retroflexus | Wild Buckwheat Polygonum convolvulus | Wild Mustard Brassica kaber | Green Foxtail Setaria viridis | Wild Oats Avena fatus | Wheat Triticum aestivum | Downy Brome Bromus tectorum |
|---|---|---|---|---|---|---|---|---|
| 1 | PRE | 4 | 4 | | 3 | 4 | 2 | 1 | 2 |
| | 2 | 4 | 4 | | 1 | 4 | 1 | 0 | 1 |
| | 1 | 4 | 4 | | 1 | 4 | 1 | 0 | 0 |
| | ½ | 2 | 2 | | 0 | 3 | 0 | 0 | 0 |

TABLE III-continued
EFFECT OF HERBICIDES ON WHEAT AND ASSOCIATED WEEDS

| Compound no. | Application | Application Rate (lb/A) | Pigweed Amaranthus retroflexus | Wild Buckwheat Polygonum convolvulus | Wild Mustard Brassica kaber | Green Foxtail Setaria viridis | Wild Oats Avena fatua | Wheat Triticum aestivum | Downy Brome Bromus tectorum |
|---|---|---|---|---|---|---|---|---|---|
|   | POST | 4 | 4 | 4 | 4 | 4 | 3 | 1 |   |
|   |   | 2 | 4 | 4 | 4 | 4 | 1 | 0 |   |
|   |   | 1 | 4 | 4 | 4 | 3 | 1 | 0 |   |
|   |   | ½ | 4 | 1 | 4 | 1 | 0 | 0 |   |
| 9 | PRE | 4 | 4 |   | 2 | 4 | 3 | 1 | 3 |
|   |   | 2 | 4 |   | 2 | 4 | 1 | 1 | 2 |
|   |   | 1 | 4 |   | 1 | 4 | 0 | 0 | 1 |
|   |   | ½ | 4 |   | 0 | 4 | 0 | 0 | 0 |
|   | POST | 4 | 4 | 4 | 4 | 4 | 3 | 1 |   |
|   |   | 2 | 4 | 4 | 4 | 4 | 1 | 0 |   |
|   |   | 1 | 4 | 4 | 4 | 3 | 1 | 0 |   |
|   |   | ½ | 4 | 4 | 4 | 2 | 1 | 0 |   |
| 12 | PRE | 4 | 4 | 3 | 4 | 2 | 1 | 1 |   |
|   |   | 2 | 4 | 1 | 4 | 1 | 0 | 1 |   |
|   |   | 1 | 3 | 1 | 4 | 0 | 0 | 1 |   |
|   |   | ½ | 1 | 0 | 2 | 0 | 0 | 0 |   |
|   | POST | 4 | 4 | 4 | 4 | 4 | 3 | 1 |   |
|   |   | 2 | 4 | 4 | 4 | 4 | 2 | 0 |   |
|   |   | 1 | 4 | 3 | 4 | 2 | 1 | 9 |   |
|   |   | ½ | 4 | 3 | 4 | 2 | 0 | 0 |   |
| 16 | POST | 4 | 4 | 4 | 4 | 4 | 3 | 1 |   |
|   |   | 2 | 4 | 4 | 4 | 4 | 2 | 0 |   |
|   |   | 1 | 4 | 4 | 4 | 3 | 2 | 0 |   |
|   |   | ½ | 3 | 3 | 4 | 2 | 1 | 0 |   |
| barban | POST | 1 | 0 |   | 0 | 0 | 4 | 0 | 1 |
|   |   | ½ | 0 |   | 0 | 0 | 4 |   | 0 |

TABLE IV
POST-EMERGENT EFFECTS OF COMBINATIONS OF HERBICIDES WITH BARBAN ON WHEAT AND ASSOCIATED WEEDS

| Compound no. | Application Rate (lb/A) | Barban Rate (lb/A) | Pigweed Amaranthus retroflexus | Downy Brome Bromus tectorum | Wild Mustard Brassica kaber | Green Foxtail Setaria viridis | Wild Oats Avena fatua | Wheat Triticum aestivum |
|---|---|---|---|---|---|---|---|---|
| 1 | 2 | ½ | 4 | 4 | 4 | 4 | 4 | 2 |
|   | 1 | ½ | 4 | 4 | 4 | 4 | 4 | 1 |
|   | ½ | ½ | 4 | 3 | 4 | 4 | 4 | 1 |
| 9 | 2 | ½ | 4 | 4 | 4 | 4 | 4 | 2 |
|   | 1 | ½ | 4 | 4 | 4 | 4 | 4 | 2 |
|   | ½ | ½ | 4 | 3 | 4 | 4 | 4 | 1 |
| 12 | 2 | ½ | 4 | 4 | 4 | 4 | 4 | 1 |
|   | 1 | ½ | 4 | 3 | 4 | 4 | 4 | 2 |
|   | ½ | ½ | 4 | 2 | 4 | 4 | 4 | 1 |
| 16 | 2 | ½ | 4 | 3 | 4 | 4 | 4 | 1 |
|   | 1 | ½ | 4 | 3 | 4 | 4 | 4 | 0 |
|   | ½ | ½ | 4 | 2 | 4 | 4 | 4 | 0 |

TABLE V
PRE-EMERGENCE USE OF HERBICIDES AGAINST SUGAR BEETS, RAPE AND ASSOCIATED WEEDS

| Compound no. | Application Rate (lg/A) | Kochia Kochia scoparia | Lambquarters Chenopodium album | Pigweed Amaranthus retroflexus | Sugar Beets Beta vulgaris | Rapeseed Brassica napus | Wild Oats Avena fatua | Green Foxtail Setaria viridis |
|---|---|---|---|---|---|---|---|---|
| 18 | 4 | 4 | 2 | 4 | 4 | 4 | 2 | 4 |
|   | 2 | 3 | 2 | 4 | 4 | 4 | 1 | 4 |
|   | 1 | 3 | 2 | 4 | 3 | 4 | 1 | 4 |
|   | ½ | 2 | 0 | 4 | 2 | 3 | 0 | 3 |
| 19 | 4 | 3 | 4 | 4 | 4 | 4 | 1 | 4 |
|   | 2 | 3 | 4 | 4 | 4 | 4 | 0 | 4 |
|   | 1 | 3 | 4 | 4 | 3 | 3 | 0 | 4 |
|   | ½ | 2 | 2 | 4 | 1 | 1 | 0 | 3 |

I claim:

1. The method of combating weeds in grain fields which comprises applying to the area where the combating effect is desired a herbicidally effective amount of a compound of the formula

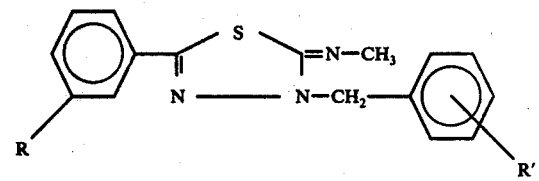

in which R is methyl or chloro and R' is hydrogen, methyl, trifluoromethyl, chloro or fluoro, said compound being applied either in unmodified form or in the form of a salt with an acid in combination with an inert carrier.

2. The method according to claim 1 which comprises applying to the area where the combating effect is desired a herbicidally effective amount of 3-benzyl-5-(3-chlorophenyl)-2-methylimino-$\Delta^4$-1,3,4-thiadiazoline in combination with an inert carrier.

3. The method according to claim 1 which comprises applying to the area where the combating effect is desired a herbicidally effective amount of 5-(3-chlorophenyl)-3-(3-methylbenzyl)-2-methylimino-$\Delta^4$-1,3,4-thiadiazoline in combination with an inert carrier.

4. The method according to claim 1 which comprises applying to the area where the combating effect is desired a herbicidally effective amount of 5-(3-chlorophenyl)-3-(4-methylbenzyl)-2-methylimino-$\Delta^4$-1,3,4-thiadiazoline in combination with an inert carrier.

5. The method according to claim 1 which comprises applying to the area where the combating effect is desired a herbicidally effective amount of 3-(3-chlorobenzyl)-2-methylimino-5-(m-tolyl)-$\Delta^4$-1,3,4-thiadiazoline in combination with an inert carrier.

6. The method according to claim 1 which comprises applying to the area where the combating effect is desired a herbicidally effective amount of 3-(4-methylbenzyl)-2-methylimino-5-(m-tolyl)-$\Delta^4$-1,3,4-thiadiazoline in combination with an inert carrier.

7. The method according to claim 1 which comprises applying to the area where the combating effect is desired a herbicidally effective amount of 5-(3-chlorophenyl)-3-(3-fluorobenzyl)-2-methylimino-$\Delta^4$-1,3,4-thiadiazoline in combination with an inert carrier.

8. The method according to claim 1 which comprises applying to the area where the combating effect is desired a herbicidally effective amount of 5-(3-chlorophenyl)-3-(4-fluorobenzyl)-2-methylimino-$\Delta^4$-1,3,4-thiadiazoline in combination with an inert carrier.

9. The method according to claim 1 which comprises applying to the area where the combating effect is desired a herbicidally effective amount of 3-(4-fluorobenzyl)-2-methylimino-5-(m-tolyl)-$\Delta^4$-1,3,4-thiadiazoline in combination with an inert carrier.

10. The method according to claim 1 which comprises applying to the area where the combating effect is desired a herbicidally effective amount of 2-methylimino-5-(m-tolyl)-3-(3-trifluoromethyl)-benzyl-$\Delta^4$-1,3,4-thiadiazoline in combination with an inert carrier.

11. The method according to claim 1 which comprises applying to the area where the combating effect is desired a herbicidally effective amount of 5-(3-chlorophenyl)-2-methylimino-3-(3-trifluoromethylbenzyl)-$\Delta^4$-1,3,4-thiadiazoline in combination with an inert carrier.

* * * * *

UNITED STATES PATENT AND TRADEMARK OFFICE
CERTIFICATE OF CORRECTION

PATENT NO. : 4,104,053
DATED : August 1, 1978
INVENTOR(S) : Norman A. Dahle (deceased)

It is certified that error appears in the above-identified patent and that said Letters Patent are hereby corrected as shown below:

Column 4, line 14 which reads "The compounds were applied to various rates, both" should read--The compounds were applied at various rates, both--to be correct.

Table III, Compound 12, Post Application Rate 1(lb/A), Wheat Column which reads "9" should read--0--to be correct.

Table III, Compound 16, Post Application Rate 2(lb/A), Wild Oats Column which reads "2" should read--3--to be correct.

Table V, Application heading reads "Application Rate (1g/A)" and should read--Application Rate (lb/A)-- to be correct.

Signed and Sealed this

Twenty-third Day of January 1979

[SEAL]

Attest:

RUTH C. MASON
Attesting Officer

DONALD W. BANNER
Commissioner of Patents and Trademarks